(12) United States Patent
Tabuchi

(10) Patent No.: US 10,016,116 B2
(45) Date of Patent: Jul. 10, 2018

(54) IMAGING DEVICE, DRIVE SIGNAL ADJUSTMENT METHOD, AND ENDOSCOPE SYSTEM

(71) Applicant: OLYMPUS CORPORATION, Tokyo (JP)

(72) Inventor: Koichiro Tabuchi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/362,109

(22) Filed: Nov. 28, 2016

(65) Prior Publication Data
US 2017/0071451 A1 Mar. 16, 2017

Related U.S. Application Data

(63) Continuation of application No. PCT/JP2015/073300, filed on Aug. 20, 2015.

(30) Foreign Application Priority Data

Oct. 7, 2014 (JP) .................................. 2014-206393

(51) Int. Cl.
*A61B 1/05* (2006.01)
*A61B 1/045* (2006.01)
(Continued)

(52) U.S. Cl.
CPC ...... *A61B 1/00071* (2013.01); *A61B 1/00006* (2013.01); *A61B 1/00009* (2013.01);
(Continued)

(58) Field of Classification Search
None
See application file for complete search history.

(56) References Cited

U.S. PATENT DOCUMENTS

| 4,667,230 A | * | 5/1987 | Arakawa | ............ H04N 5/23203 348/76 |
| 4,845,555 A | * | 7/1989 | Yabe | .................. H04N 5/23203 348/72 |

(Continued)

FOREIGN PATENT DOCUMENTS

| JP | H08-280611 A | 10/1996 |
| JP | 2003-052627 A | 2/2003 |

(Continued)

OTHER PUBLICATIONS

International Search Report dated Nov. 17, 2015 issued in PCT/JP2015/073300.

*Primary Examiner* — John P Leubecker
(74) *Attorney, Agent, or Firm* — Scully, Scott, Murphy & Presser, P.C.

(57) ABSTRACT

An imaging device includes: an imaging unit; a drive signal generation unit configured to generate and output a plurality of drive signals for driving the imaging unit; a differential converter configured to convert one of the plurality of drive signals into a differential signal; a pair of signal lines configured to transmit the differential signal and configured such that impedance matching does not occur at a terminal of one of the pair of signal lines; and an adjustment unit configured to send a detecting signal to the one of the pair of signal lines, and to adjust characteristics of at least one of the plurality of drive signals based on a time period from when the detecting signal is sent until the detecting signal is reflected and returned from the terminal of the one of the pair of signal lines.

5 Claims, 7 Drawing Sheets

(51) Int. Cl.
*A61B 1/00* (2006.01)
*A61B 1/04* (2006.01)
*H04N 7/18* (2006.01)

(52) U.S. Cl.
CPC ...... *A61B 1/00036* (2013.01); *A61B 1/00114* (2013.01); *A61B 1/00124* (2013.01); *A61B 1/04* (2013.01); *A61B 1/045* (2013.01); *H04N 7/18* (2013.01); *H04N 7/183* (2013.01)

(56) References Cited

U.S. PATENT DOCUMENTS

| | | | | |
|---|---|---|---|---|
| 5,539,333 | A * | 7/1996 | Cao | G06F 1/10 326/17 |
| 7,239,169 | B2 * | 7/2007 | Isa | H04L 25/0278 326/30 |
| 7,365,768 | B1 * | 4/2008 | Ono | A61B 1/042 348/65 |
| 2006/0114986 | A1 * | 6/2006 | Knapp, II | A61B 1/00103 375/240.01 |
| 2006/0245381 | A1 * | 11/2006 | Baxter | G06F 13/4265 370/296 |
| 2011/0013078 | A1 * | 1/2011 | Shinozaki | H04N 5/23203 348/375 |
| 2012/0016202 | A1 * | 1/2012 | Baum | A61B 1/00114 600/182 |
| 2013/0141557 | A1 * | 6/2013 | Kawata | A61B 1/00006 348/65 |
| 2014/0340496 | A1 * | 11/2014 | Okawa | A61B 1/00006 348/65 |
| 2015/0049848 | A1 * | 2/2015 | Morita | H04L 7/0337 375/354 |
| 2016/0018252 | A1 * | 1/2016 | Hanson | G01G 19/024 73/774 |

FOREIGN PATENT DOCUMENTS

| | | |
|---|---|---|
| JP | 2009-045113 A | 3/2009 |
| JP | 2009-106343 A | 5/2009 |

* cited by examiner

IMAGING DEVICE, DRIVE SIGNAL ADJUSTMENT METHOD, AND ENDOSCOPE SYSTEM

CROSS REFERENCES TO RELATED APPLICATIONS

This application is a continuation of PCT international application Ser. No. PCT/JP2015/073300, filed on Aug. 20, 2015 which designates the United States, incorporated herein by reference, and which claims the benefit of priority from Japanese Patent Application No. 2014-206393, filed on Oct. 7, 2014, incorporated herein by reference.

BACKGROUND

1. Technical Field

The disclosure relates to an imaging device for imaging an object to generate an imaging signal, a drive signal adjustment method that is performed by the imaging device, and an endoscope system.

2. Related Art

Conventionally, an endoscope system is used in the medical field for observing an organ of a subject such as a patient. The endoscope system includes an endoscope (scope) and a processing device (processor). The endoscope includes an insertion portion formed in a flexible elongated shape, a distal end of which is provided with an imaging sensor. The insertion portion is inserted into a body cavity of the subject. The processing device is coupled to the insertion portion via a cable and a connector to perform an image process on an in-vivo image captured by the imaging sensor. The processing device causes a display device to display the in-vivo image. For example, power or a signal is supplied from the processing device to the imaging sensor at the distal end of the insertion portion.

In recent years, application of an imaging sensor having a large number of pixels that enables the observation of a clearer image to the endoscope has been considered, and a small diameter of the insertion portion has been required in consideration of easiness of introduction of the endoscope into the subject. In order to realize a small diameter of the insertion portion, an inner transmission cable needs to be made thinner. When the transmission cable is made thinner, however, electric resistance of the transmission cable is increased, whereby an attenuation rate of a drive signal such as a power supply signal and a clock signal is increased. In addition, since the length and the thickness of the transmission cable vary in accordance with a kind of the endoscope, an attenuation amount of the drive signal changes depending on the endoscope. A value of the drive signal is conventionally set at a relatively high level so that the value can be applied to all kinds of endoscopes. However, exact adjustment of the value of the drive signal that depends on the endoscope has been required so as to be able to deal with prevention of heat generation due to a reduction in the voltage of the imaging sensor and an increase in speed of signal transmission.

In this regard, an endoscope system including a voltage detection unit has been proposed (for example, refer to JP 2009-106343 A). Specifically, the voltage detection unit that detects voltage values at two points including an imaging unit and a driver circuit is newly provided at a distal end of an insertion portion of an endoscope, and the voltage that is applied to the endoscope is adjusted on the basis of the voltage values detected in the voltage detection unit when power is supplied.

SUMMARY

In some embodiments, an imaging device includes: an imaging unit; a drive signal generation unit configured to generate and output a plurality of drive signals for driving the imaging unit; a differential converter configured to convert one of the plurality of drive signals into a differential signal; a pair of signal lines configured to transmit the differential signal and configured such that impedance matching does not occur at terminal of one of the pair of signal lines; and an adjustment unit configured to send a detecting signal to the one of the pair of signal lines, and to adjust characteristics of at least one of the plurality of drive signals based on a time period from when the detecting signal is sent until the detecting signal is reflected and returned from the terminal of the one of the pair of signal lines.

In some embodiments, a drive signal adjustment method is performed by an imaging device having a pair of signal lines configured to transmit, as a differential signal, one of a plurality of drive signals and configured such that impedance matching does not occur at a terminal of one of the pair of signal lines. The method includes: sending a detecting signal to the one of the pair of signal lines, and acquiring a return time period that is a time period from when the detecting signal is sent until the detecting signal is reflected and returned from the terminal of the one of the pair of signal lines; and adjusting characteristics of at least one of the plurality of drive signals based on the return time period.

In some embodiments, an endoscope system includes: an insertion portion configured to be inserted into a subject; a processing device to which the insertion portion is detachably connected; an imaging unit provided at a distal end of the insertion portion; a drive signal generation unit configured to generate and output a plurality of drive signals for driving the imaging unit; a differential converter configured to convert one of the plurality of drive signals into a differential signal; a pair of signal lines configured to transmit the differential signal and configured such that impedance matching does not occur at a terminal of one of the pair of signal lines; and an adjustment unit configured to send a detecting signal to the one of the pair of signal lines, and to adjust characteristics of at least one of the plurality of drive signals based on a time period from when the detecting signal is sent until the detecting signal is reflected and returned from the terminal of the one of the pair of signal lines.

The above and other features, advantages and technical and industrial significance of this invention will be better understood by reading the following detailed description of presently preferred embodiments of the invention, when considered in connection with the accompanying drawings.

DETAILED DESCRIPTION

Hereinafter, as modes for carrying out the present invention (hereinafter referred to as "embodiment(s)"), an endoscope system will be described. The present invention is not limited by the embodiments. The same reference signs are used to designate the same elements throughout the drawings.

Embodiments

Figure 1:
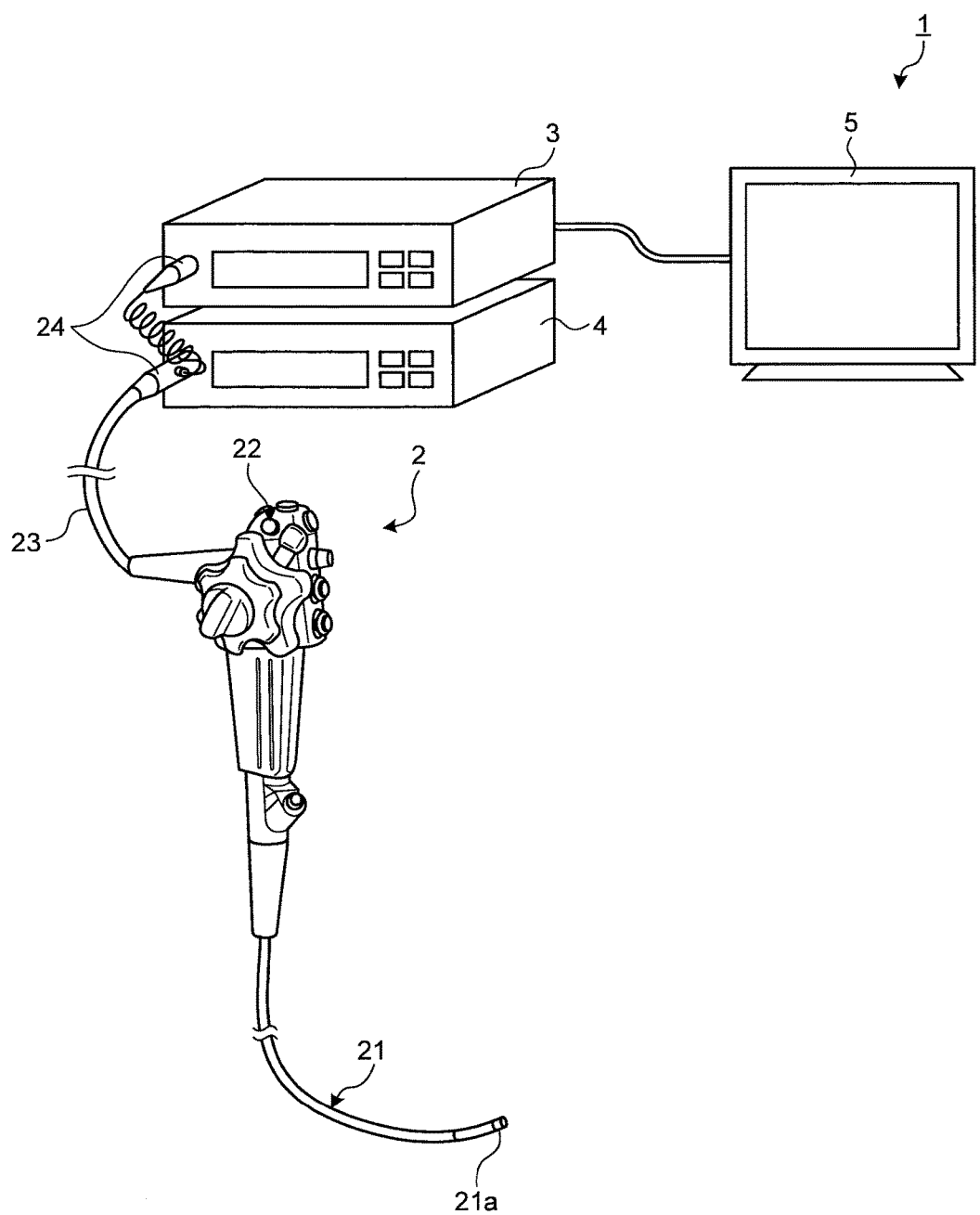
FIG. 1 is a schematic view illustrating an overview configuration of an endoscope system according to an embodiment of the present invention.
Figure 2:
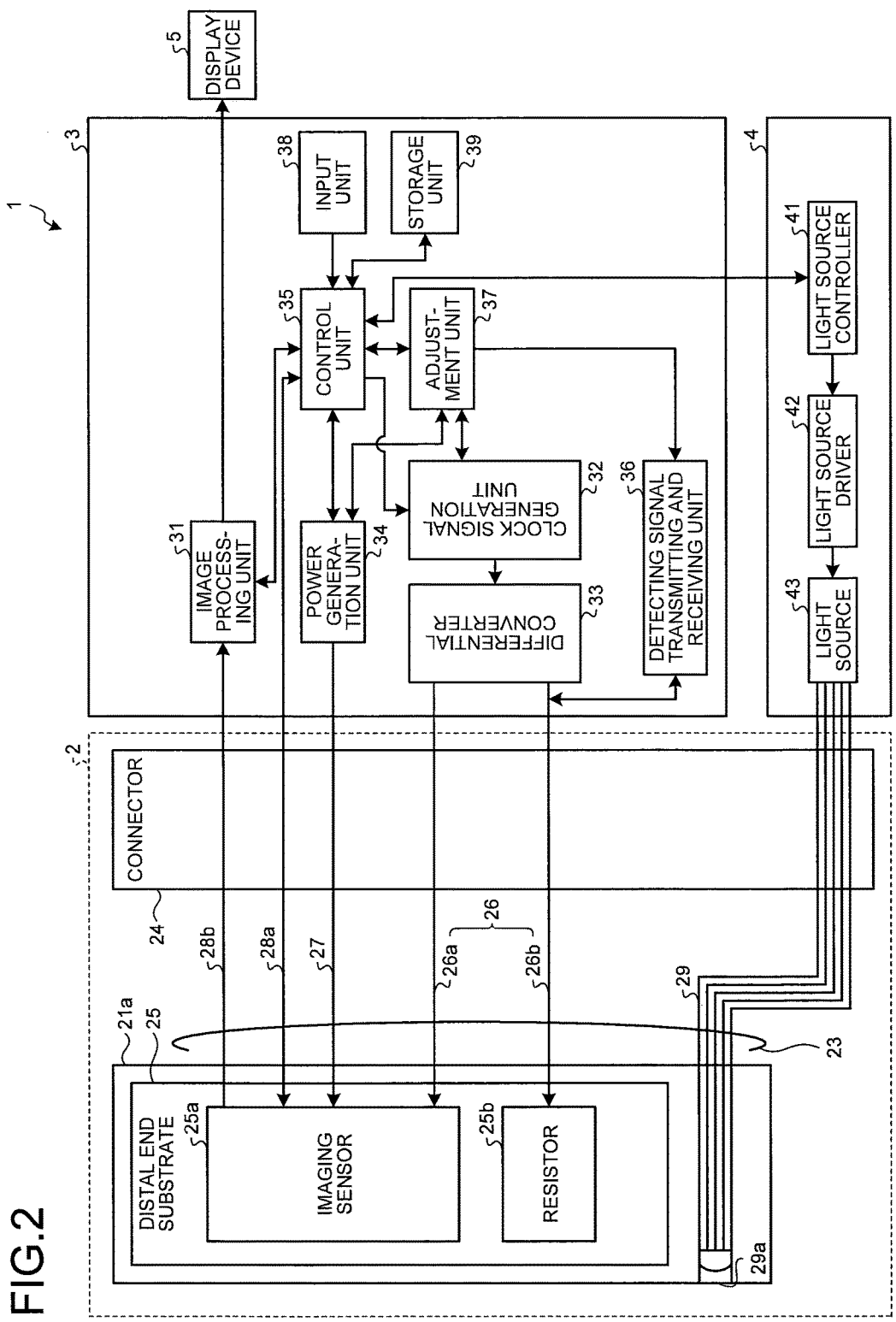
FIG. 2 is a block diagram schematically illustrating a configuration of the endoscope system illustrated in FIG. 1.

FIG. 1 is a schematic view illustrating an overview configuration of an endoscope system according to an embodiment of the present invention. FIG. 2 is a block diagram schematically illustrating a configuration of the endoscope system illustrated in FIG. 1. As illustrated in FIGS. 1 and 2, an endoscope system 1 according to the embodiment includes an endoscope 2 (scope), a processing device 3, a light source device 4, and a display device 5. The endoscope 2 is introduced into a subject, and captures the inside of a body of the subject to generate an image signal of the inside of the subject. The processing device 3 performs a predetermined image process on the image signal captured by the endoscope 2, and controls each part of the endoscope system 1. The light source device 4 generates illumination light (observation light) of the endoscope 2. The display device 5 displays an image corresponding to the image signal subjected to the image process by the processing device 3.

The endoscope 2 includes an insertion portion 21, an operating unit 22, a universal code 23, and a connector 24. The insertion portion 21 is formed in a flexible elongated shape. The operating unit 22 is connected to a proximal end side of the insertion portion 21, and accepts input of various operation signals. The universal code 23 extends from the operating unit 22 in a direction different from a direction in which the insertion portion 21 extends. A plurality of cables connected to the processing device 3 or the light source device 4 is incorporated in the universal code 23. The connector 24 is provided at a proximal end portion of the universal code 23, and freely attached to or detached from the processing device 3 and the light source device 4. The connector 24 sends and receives an electric signal to and from the processing device 3, and causes light emitted by the light source device 4 to pass through the connector 24. Signal cables 26a, 26b, 27, 28a, and 28b incorporated in the insertion portion 21 and the universal code 23 constitute a part of a transmission path for a signal in the endoscope 2 and the processing device 3. The signal cables 26a and 26b (a pair of signal lines) constitute a pair of differential signal cables 26 that is a coaxial wire.

A distal end portion 21a of the insertion portion 21 is provided with a distal end substrate 25 on which an imaging sensor 25a (imaging unit) and a resistor 25b are mounted. The imaging sensor 25a performs photoelectric conversion on received light to generate an imaging signal. A distal end portion of a light guide cable 29 is inserted into the distal end portion 21a. The light guide cable 29 forms a light guide path for the light emitted by the light source device 4. An optical system for light collection is provided on a light receiving surface side of the imaging sensor 25a. An optical system for illumination is provided on a distal end side of the light guide cable 29, and an object is illuminated with the light emitted from the light source device 4 through an illumination window 29a.

The imaging sensor 25a has, for example, a plurality of pixels arranged in a two-dimensional matrix form. The imaging sensor 25a includes a sensor unit and an image sensor. The sensor unit performs photoelectric conversion on the received light and outputs an electric signal (image signal). The image sensor has an analog front end (AFE) that performs a noise removal or an A/D conversion on the electric signal output from the sensor unit. The image sensor is, for example, a solid state imaging sensor such as a complementary metal oxide semiconductor (CMOS) and a charge coupled device (CCD). An optical system (not illustrated) such as an objective lens is arranged on a light receiving surface side of the sensor unit of the imaging sensor 25a. The image signal (digital) generated by the imaging sensor 25a is output to the processing device 3 through the signal cable 28b and the connector 24. A terminal of the signal cable 26a that is one of the pair of differential signal cables 26 is connected to the imaging sensor 25a. The pair of differential signal cables 26 outputs a differential signal from a differential converter 33 which will be described later.

The signal cable 26b that is the other of the pair of differential signal cables 26 is connected to the resistor 25b. The pair of differential signal cables 26 outputs the differential signal from the differential converter 33 which will be described later. The resistor 25b is set to a resistance value equal to or greater than, for example, 1 MΩ such that impedance matching does not occur at the terminal of the signal cable 26b.

The processing device 3 includes an image processing unit 31, a clock signal generation unit 32 (drive signal generation unit), the differential converter 33, a power generation unit 34 (drive signal generation unit), a control unit 35, a detecting signal transmitting and receiving unit 36, an adjustment unit 37, an input unit 38, and a storage unit 39.

The image processing unit 31 performs a predetermined image process on the imaging signal sent from the endoscope 2. The image processing unit 31 performs, on the image signal output from the imaging sensor 25a, at least a part of processes including, for example, a synchronizing process, a white balance (WB) adjustment process, a gain adjustment process, a gamma correction process, an edge enhancement process, and a format conversion process or the like. The image processing unit 31 includes a field programmable gate array (FPGA) or the like.

The clock signal generation unit 32 generates a clock signal that is one of drive signals for driving the imaging sensor 25a. The clock signal generation unit 32 generates the clock signal that serves as a reference for operation. The clock signal generated by the clock signal generation unit 32 serves as a reference for operation of at least the imaging sensor 25a of the distal end portion 21a.

The differential converter 33 converts a single clock signal input from the clock signal generation unit 32 into a differential signal, i.e., two clock signals having inverted phases with respect to each other. The differential converter 33 then outputs the clock signals to the respective signal cables 26a and 26b of the differential signal cables 26. In other words, in the embodiment, as a method of sending the clock signal from the clock signal generation unit 32 to the imaging sensor 25a, a method of transferring a single signal using the pair of differential signal cables (differential signal line) 26 is used (differential transmission). Voltages of the pair of respective differential signal cables are set positive (+) and negative (−, phase inversion), whereby noise which is likely to be mixed in each line can be cancelled. Therefore, resistance to the noise is strong, and a fast transfer is enabled as compared with a single end signal. The terminal of the signal cable 26a that is one of the pair of two differential signal cables 26 is connected to the imaging sensor 25a. The terminal of the signal cable 26b that is the other of the differential signal cables 26 is connected to the resistor 25b, and does not land at other circuits. In other words, the impedance matching does not occur at the terminal of the signal cable 26b, and the signal sent to the signal cable 26b is reflected from the terminal of the signal cable 26b and returned to the original place. In order to prevent accumulation of heat, the terminal of the signal cable 26b only needs to be processed so that the signal sent to the signal cable 26b is reflected from the terminal of the signal cable 26b and returned to the original place. Therefore, the terminal of the signal cable 26b does not necessarily need to be connected to the resistor 25b. The terminal of the signal cable 26b may be fully opened, may be in an electrically floating state in which the terminal of the signal cable 26b is not connected to any circuit, or may only be connected to the distal end portion 21a.

The power generation unit 34 generates a power supply voltage, and supplies the generated power supply voltage to each part of the endoscope 2 through the connector 24 and the universal code 23. In FIG. 2, the power generation unit 34 generates a power supply signal that is one of the drive signals for driving the imaging sensor 25a, and supplies the generated power supply signal to the imaging sensor 25a through the signal cable 27.

The control unit 35 performs overall control of the endoscope system 1 including the processing device 3. The control unit 35 includes, for example, an FPGA in which a central processing unit (CPU) or the like is embedded. The control unit 35, for example, transfers instruction information or data to each section of the processing device 3, thereby controlling the operation of the endoscope system 1. The control unit 35 is coupled to each component of the processing device 3, the imaging sensor 25a, and the light source device 4 via respective signal cables.

The detecting signal transmitting and receiving unit 36 sends a detecting signal to the signal cable 26b of the differential signal cables 26, and receives and reads the detecting signal reflected and returned from the terminal of the signal cable 26b. The detecting signal transmitting and receiving unit 36 sends and receives an impulse signal. Since the terminal of the signal cable 26b is connected to only the resistor 25b, functions of the imaging sensor 25a and other elements are not affected even when the impulse signal is sent. A dedicated circuit for the sending and receiving does not need to be particularly provided as the detecting signal transmitting and receiving unit 36, and it is sufficient to make a determination using an edge by means of an FPGA or the like.

The detecting signal is sent to the signal cable 26b by the detecting signal transmitting and receiving unit 36, and the adjustment unit 37 adjusts at least one of a plurality of drive signals based on a time period from when the detecting signal is sent until the detecting signal is reflected and returned from the terminal of the signal cable 26b. More specifically, the adjustment unit 37 changes amplitude of the clock signal generated by the clock signal generation unit 32. The adjustment unit 37 changes voltage of the power supply signal generated by the power generation unit 34. The adjustment unit 37 includes, for example, a CPU.

The input unit 38 is realized by using an operation device such as a mouse, a keyboard, and a touch panel, and accepts input of various types of instruction information for the endoscope system 1. More specifically, the input unit 38 accepts the input of the various types of instruction information such as subject information (e.g., an ID, a date of birth, and a name or the like), identification information of the endoscope 2 (e.g., an ID and an item to be examined), and examination contents.

The storage unit 39 stores data including, for example, various programs for operating the endoscope system 1 and various parameters required for the operation of the endoscope system 1. The storage unit 39 includes a random access memory (RAM) and a read only memory (ROM) or the like. The storage unit 39 may store the image signal output by the imaging sensor 25a. The storage unit 39 may include a memory card or the like attached from the outside of the processing device 3.

The light source device 4 has a light source controller 41, a light source driver 42, and a light source 43. The light source controller 41 controls an emission process for the illumination light of the light source 43 under the control of the control unit 35. The light source driver 42 supplies predetermined power to the light source 43 under the control of the light source controller 41. The light source 43 includes, for example, a light source such as a white LED that emits white light and an optical system such as a condenser lens. The light source 43 generates the illumination light that is supplied to the endoscope 2. The object is illuminated, through the illumination window 29a, with the light emitted from the light source 43 at the distal end portion 21a of the insertion portion 21 via the connector 24 and the universal code 23 by the light guide cable 29. The imaging sensor 25a is arranged in the vicinity of the illumination window 29a.

The display device 5 receives image data generated by the processing device 3 from the processing device 3, and displays an image corresponding to the image data. The display device 5 is provided with a display panel including a liquid crystal or organic electro luminescence (EL).

Figure 3:
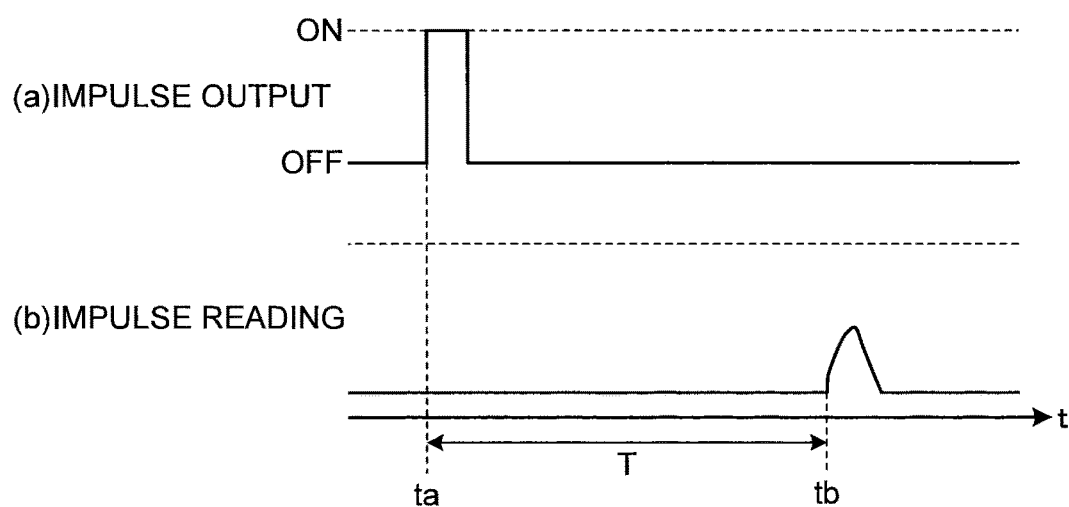
FIG. 3 is a timing chart illustrating impulse signal output and impulse signal reading that are performed by a detecting signal transmitting and receiving unit illustrated in FIG. 2.

FIG. 3 is a timing chart illustrating impulse signal output and impulse signal reading (reception) that are performed by the detecting signal transmitting and receiving unit 36. A return time period T of the impulse signal is a time period from when the impulse signal is output at time to from the detecting signal transmitting and receiving unit 36 to the signal cable 26b until the impulse signal is reflected from the terminal of the signal cable 26b and returned at time tb. The return time period T varies depending on a propagation speed in a copper wire of the signal cable 26b, a thickness of the copper wire, a temperature value within the endoscope 2, and a cable length of the signal cable 26b. Among them, the propagation speed in the copper wire of the signal cable 26b and the thickness of the copper wire can be determined by the ID of the endoscope 2. Since the endoscope 2 is generally used at a controlled constant temperature, an initial value of the temperature within the endoscope 2 can also be set. Therefore, if the return time period T of the impulse signal is obtained, the cable length of the signal cable 26b can be acquired. If the cable length of the signal cable 26b is obtained, an attenuation amount of the clock signal in the signal cable 26b can be calculated. The attenuation amount of the clock signal transmitted through the signal cable 26b can be regarded as being equivalent to an attenuation amount of the clock signal transmitted through the signal cable 26a having the same length as the signal cable 26b. Therefore, if the attenuation amount of the clock signal in the signal cable 26b is obtained, it is possible to acquire an amplitude value of the clock signal that is output to the signal cable 26a in order to transmit the clock signal to the imaging sensor 25a with an optimal amplitude value.

In this regard, in the embodiment, a predetermined arithmetic expression is obtained in advance for each type of the endoscope 2. The propagation speed of the copper wire of the signal cable 26b of the endoscope 2, the thickness of the copper wire, and the initial value of the temperature within the endoscope 2 are reflected in the predetermined arithmetic expression, and the return time period T is applied to the predetermined arithmetic expression, whereby the amplitude value for the output of the clock signal corresponding to the return time period T can be computed from the cable length of the signal cable corresponding to the return time period T. The adjustment unit 37 refers to the arithmetic expression corresponding to the type of the endoscope 2 based on the ID of the endoscope 2 attached to the processing device 3, and applies the return time period T to the arithmetic expression which the adjustment unit 37 has referred to. Consequently, the adjustment unit 37 acquires the amplitude value for the output of the clock signal. Then, the adjustment unit 37 controls the clock signal generation unit 32 so that the clock signal generation unit 32 outputs the clock signal having the amplitude value acquired by the computation. It is understood that the longer the return time period T of the detecting signal in the signal cable 26b is, the relatively longer the cable length of the signal cable 26b is. In this case, therefore, the adjustment unit 37 relatively increases the amplitude value of the clock signal. On the other hand, it is understood that the shorter the return time period T is, the relatively shorter the cable length of the signal cable 26b is. In this case, therefore, the adjustment unit 37 relatively reduces the amplitude value of the clock signal.

The length of the signal cable 26b is equal to the length of each of the other signal cables 26a, 27, 28a, and 28b constituting the universal code 23 due to the device configuration of the endoscope 2. With regard to the other signal cables as well, a propagation speed of a copper wire of each signal cable and a thickness of the copper wire can be determined by the ID of the endoscope 2, and an initial value of a temperature within the endoscope 2 can also be set. Therefore, when the cable length of the signal cable 26b is obtained, an attenuation amount of each of the various drive signals propagated through the other signal cables can also be calculated.

More specifically, among the drive signals, an attenuation amount of the power supply signal propagated through the signal cable 28a can also be calculated. Therefore, a voltage value of the power supply signal that is output to the signal cable 28a for causing the power supply signal to reach the imaging sensor 25a with an optimal voltage value can be acquired. When the propagation speed of the copper wire of the signal cable 26b of the endoscope 2, the thickness of the copper wire, and the initial value of the temperature within the endoscope 2 are reflected, and the return time period T is applied, the cable length of the signal cable 26b corresponding to the return time period T, namely, a cable length of the signal cable 28a, can be acquired. Furthermore, when the computed length of the signal cable 28a, a propagation speed of a copper wire of the signal cable 28a, and a thickness of the copper wire of the signal cable 28a are applied, the attenuation amount of the power supply signal propagated through the signal cable 28a is calculated, and the voltage value for the output of the power supply signal for causing the power supply signal to reach the imaging sensor 25a with the optimal voltage value is calculated. A predetermined arithmetic expression in which each of these parameters is reflected is obtained in advance for each type of the endoscope 2. When the return time period T is applied to the predetermined arithmetic expression, the voltage value for the output of the power supply signal can be computed. The adjustment unit 37 refers to the arithmetic expression corresponding to the type of the endoscope 2 based on the ID of the endoscope 2 attached to the processing device 3, and applies the return time period T to the arithmetic expression which the adjustment unit 37 has referred to. Consequently, the adjustment unit 37 acquires the voltage value for the output of the power supply signal. The adjustment unit 37 controls the power generation unit 34 so that the power generation unit 34 outputs the power supply signal having the voltage value acquired by the computation. The longer the return time period T of the detecting signal in the signal cable 26b is, the relatively longer the cable length of the signal cable 26b is. In this case, therefore, the adjustment unit 37 relatively increases the voltage value of the power supply signal for the output. On the other hand, the shorter the return time period T is, the relatively shorter the cable length of the signal cable 26b is. In this case, therefore, the adjustment unit 37 relatively reduces the voltage value of the power supply signal for the output.

Figure 4:
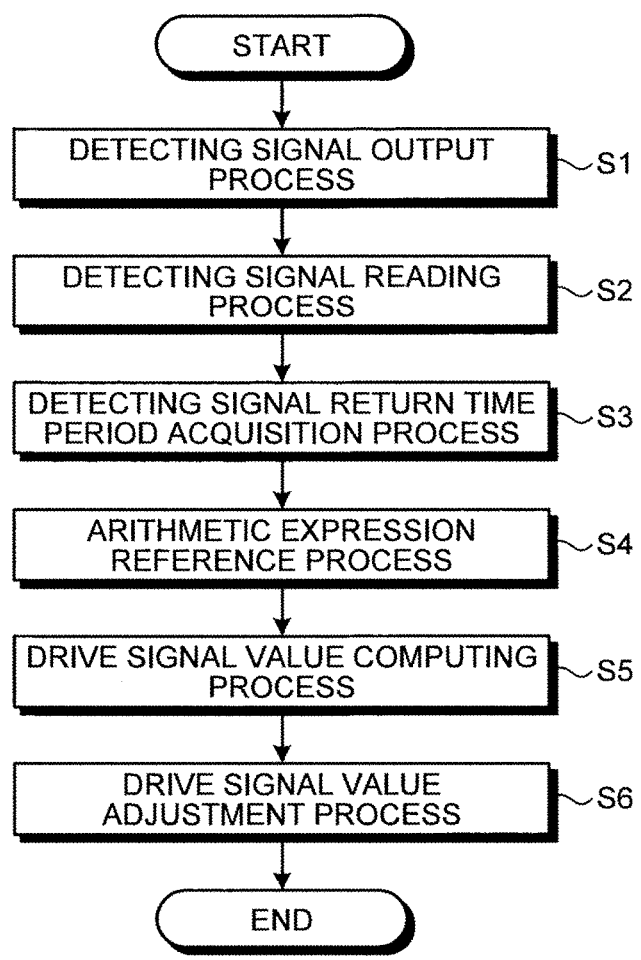
FIG. 4 is a flowchart illustrating a processing procedure for a drive signal adjustment method that is performed by the endoscope system illustrated in FIG. 2.

FIG. 4 is a flowchart illustrating a processing procedure for a drive signal adjustment method that is performed by the endoscope system 1. As illustrated in FIG. 4, the detecting signal transmitting and receiving unit 36 performs, under the control of the adjustment unit 37, a detecting signal output process of outputting the detecting signal to the signal cable 26b (step S1), and performs a detecting signal reading process of reading the detecting signal reflected and returned from the terminal of the signal cable 26b (step S2). The detecting signal is sent to the signal cable 26b by the detecting signal transmitting and receiving unit 36, and the adjustment unit 37 performs a detecting signal return time period acquisition process of acquiring the return time period of the detecting signal that is the time period from when the detecting signal is sent until the detecting signal is reflected and returned from the terminal of the signal cable 26b (step S3).

The adjustment unit 37 performs an arithmetic expression reference process of referring to the arithmetic expression that depends on the type of the endoscope 2 based on the ID of the endoscope 2 attached to the processing device 3 (step S4). More specifically, the adjustment unit 37 refers to a first arithmetic expression for acquiring the amplitude value for the output of the clock signal and a second arithmetic expression for acquiring the voltage value for the output of the power supply signal to the imaging sensor 25a. These arithmetic expressions are held in, for example, a memory (not illustrated) included in the endoscope 2. The adjustment unit 37 reads each arithmetic expression from the memory of the endoscope 2 when the endoscope 2 is attached to the processing device 3. Alternatively, these arithmetic expressions may be stored in the storage unit 39 within the processing device 3. Alternatively, these arithmetic expressions may be stored in an external database which is not illustrated, and the adjustment unit 37 may be coupled to the external database via a network line which is not illustrated, and refer to each arithmetic expression.

The adjustment unit 37 applies the acquired return time period of the detecting signal to the arithmetic expression which the adjustment unit 37 has referred to, whereby the adjustment unit 37 performs a drive signal value computing process of computing the value of the drive signal to be adjusted (step S5). More specifically, the adjustment unit 37 applies the return time period of the detecting signal to the first arithmetic expression, whereby the adjustment unit 37 computes the amplitude value for the output of the clock signal. The adjustment unit 37 also applies the return time period of the detecting signal to the second arithmetic expression, whereby the adjustment unit 37 computes the voltage value for the output of the power supply signal.

The adjustment unit 37 performs a drive signal value adjustment process of adjusting the drive signal generation unit so that the drive signal generation unit outputs the drive signal with the value computed in the computing process in step S5 (step S6). More specifically, the adjustment unit 37 changes the amplitude value of the clock signal that is output by the clock signal generation unit 32 to the amplitude value acquired by the computing process with the use of the first arithmetic expression. The adjustment unit 37 changes the voltage value of the power supply signal that is output by the power generation unit 34 to the voltage value acquired by the computing process with the use of the second arithmetic expression. The adjustment unit 37 performs the processes of respective steps S1 to S6, whereby the adjustment unit 37 automatically adjusts, for each endoscope 2, the value of the drive signal that is appropriate for the endoscope 2 attached to the processing device 3.

Figure 5:
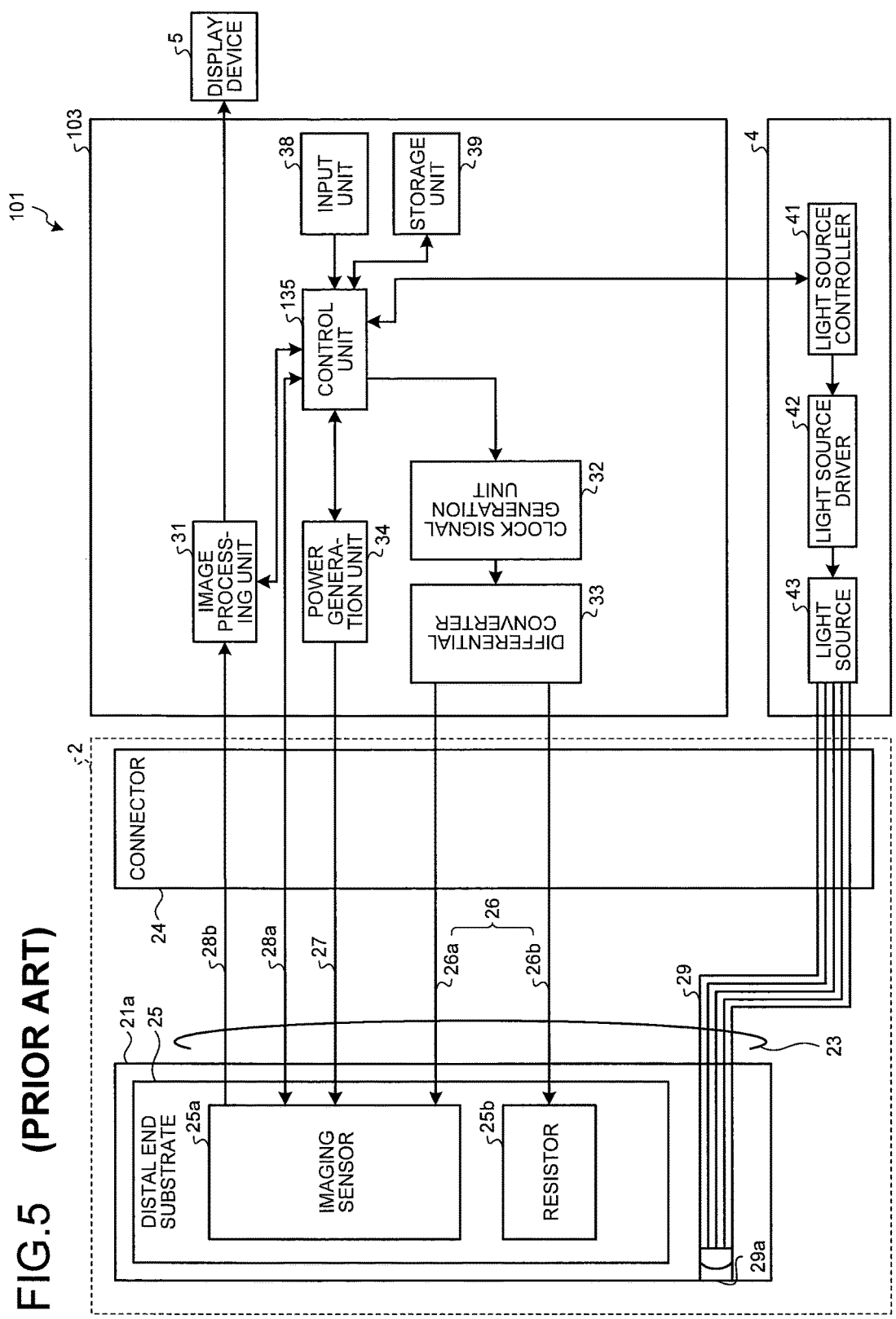
FIG. 5 is a block diagram schematically illustrating a configuration of an endoscope system according to a conventional technique.

FIG. 5 is a block diagram schematically illustrating a configuration of an endoscope system according to a conventional technique. As illustrated in FIG. 5, a conventional endoscope system 101 also employs the differential transmission that uses the differential converter 33 and the two differential signal cables 26 as the method of sending the clock signal from the clock signal generation unit 32 of a processing device 103 controlled by a control unit 135 to the imaging sensor 25*a* of the distal end portion 21*a* of the endoscope 2, whereby noise resistance is enhanced. The terminal of the signal cable 26*a* that is one of the differential signal cables 26 is connected to the imaging sensor 25*a*. Since the imaging sensor 25*a* at the distal end operates even by means of a single clock, the terminal of the other signal cable 26*b* is not connected to the imaging sensor 25*a*. Although the signal cable 26*b* is connected to the resistor 25*b* of the distal end substrate 25 in the example in FIG. 5, the signal cable 26*b* does not land at other circuits. Therefore, the signal cable 26*b* is in a high impedance state and not used even though the clock signal is transmitted to the distal end portion 21*a*.

In the embodiment, the detecting signal is sent from a side where the processing device 3 exists to the signal cable 26*b* that is one of the differential signal cables 26 and has not been used in the conventional technique. Then, the signal reflected and returned from the distal end is read, and the return time period is calculated, whereby the value of at least one drive signal is computed. In the embodiment, therefore, a signal cable for acquiring the return time period of the detecting signal does not need to be newly provided within the insertion portion of the endoscope 2. In addition, in the embodiment, the detecting signal transmitting and receiving unit 36 is provided on a side where the processing device 3 exists, and the value of the drive signal is adjusted in the adjustment unit 37 within the processing device 3. Therefore, a detecting circuit does not need to be newly provided at the distal end of the endoscope 2. In other words, in the embodiment, the configuration of the distal end of the insertion portion 21 of the endoscope 2 can be kept similar to the conventional configuration. Therefore, according to the embodiment, while achieving a small diameter of the insertion portion 21 of the endoscope 2, the value of the drive signal that is appropriate for the endoscope 2 attached to the processing device 3 can be automatically and exactly adjusted for each endoscope 2 when the adjustment unit 37 performs the respective processes of steps S1 to S6 illustrated in FIG. 4. Consequently, it is possible to adequately deal with prevention of heat generation due to a reduction in the voltage of the imaging sensor 25*a* and an increase in speed of signal transmission. A dedicated circuit for the sending and receiving does not need to be particularly provided as the detecting signal transmitting and receiving unit 36, and it is sufficient to determine the return time period of the detecting signal using the edge by means of the FPGA or the like. Therefore, a large circuit change does not need to be particularly performed on a side where the processing device 3 exists as well.

Moreover, in the embodiment, the adjustment unit 37 performs the processes of steps S1 to S6 illustrated in FIG. 4 mainly every time the endoscope system 1 is activated, whereby the adjustment unit 37 can supply the power supply signal having the fair voltage value and the clock signal having the fair amplitude value to the imaging sensor 25*a* from the beginning of the examination. Needless to say, the adjustment unit 37 may perform the respective processes of steps S1 to S6 illustrated in FIG. 4 when the power of the endoscope system 1 stops, or regularly after the examination is started. Alternatively, the adjustment unit 37 may perform the respective processes of steps S1 to S6 illustrated in FIG. 4 when a temperature sensor (not illustrated) gives a high temperature warning.

Figure 6:
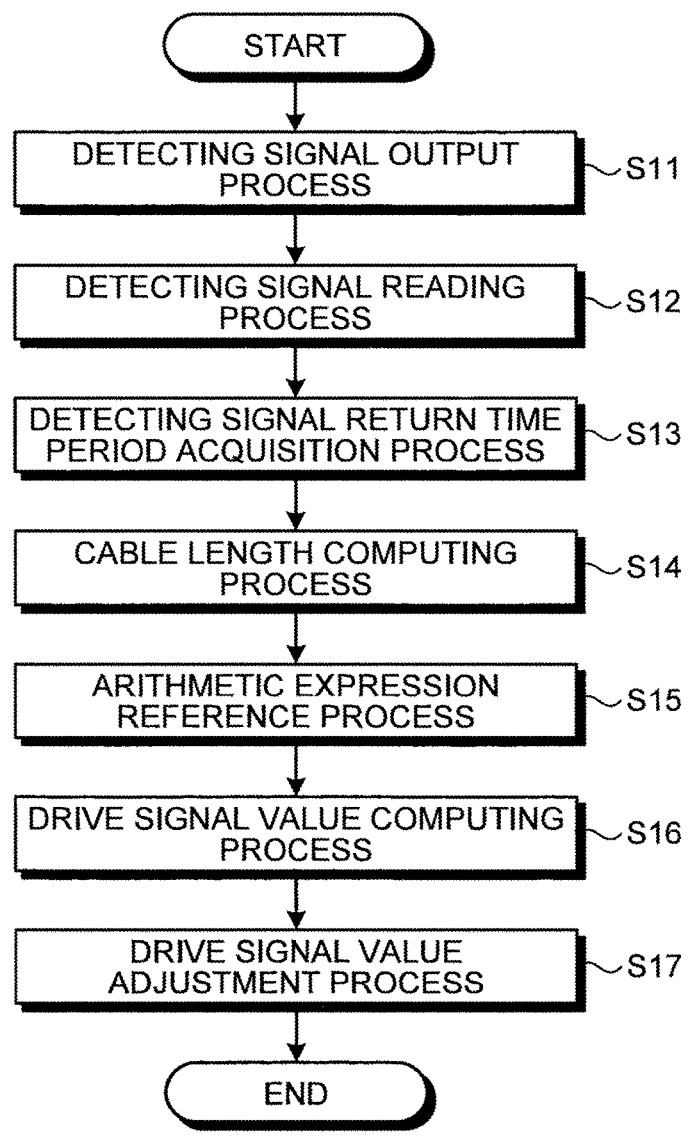
FIG. 6 is a flowchart illustrating another processing procedure for the drive signal adjustment method that is performed by the endoscope system illustrated in FIG. 2.

FIG. 6 is a flowchart illustrating another processing procedure for the drive signal adjustment method that is performed by the endoscope system 1. Steps S11 to S13 illustrated in FIG. 6 are steps S1 to S3 illustrated in FIG. 4. The adjustment unit 37 performs a cable length computing process of computing the cable length of the signal cable 26*b* based on the propagation speed of the copper wire of the signal cable 26*b*, the thickness of the copper wire, the initial value of the temperature within the endoscope 2, and the return time period T (step S14). Since the propagation speed of the copper wire of the signal cable 26*b* and the thickness of the copper wire can be acquired on the basis of the ID of the endoscope 2, the adjustment unit 37 applies the return time period T to the predetermined arithmetic expression that uses the propagation speed of the copper wire of the signal cable 26*b*, the thickness of the copper wire, and the initial value of the temperature within the endoscope 2 as the parameters. The adjustment unit 37 thus computes the cable length of the signal cable 26*b*. The adjustment unit 37 performs an arithmetic expression reference process of referring to the arithmetic expression for acquiring the drive signal value (step S15). For example, the arithmetic expression is stored in the storage unit 39 within the processing device 3. The adjustment unit 37 refers to the arithmetic expression by which the amplitude value for the output of the clock signal can be computed by means of the application of the cable length of the signal cable 26*b*, and the arithmetic expression by which the voltage value for the output of the power supply signal to the imaging sensor 25*a* can be computed by means of the application of the cable length of the signal cable 26*b*. The adjustment unit 37 applies the cable length of the signal cable 26*b* to the arithmetic expression which the adjustment unit 37 has referred to, whereby the adjustment unit 37 performs a drive signal value computing process of computing the value of the drive signal to be adjusted (step S16). Step S17 illustrated in FIG. 6 is step S6 illustrated in FIG. 4. As described above, the adjustment unit 37 may compute, after calculating the cable length of the signal cable 26*b*, the value of each drive signal based on the calculated cable length.

Figure 7:
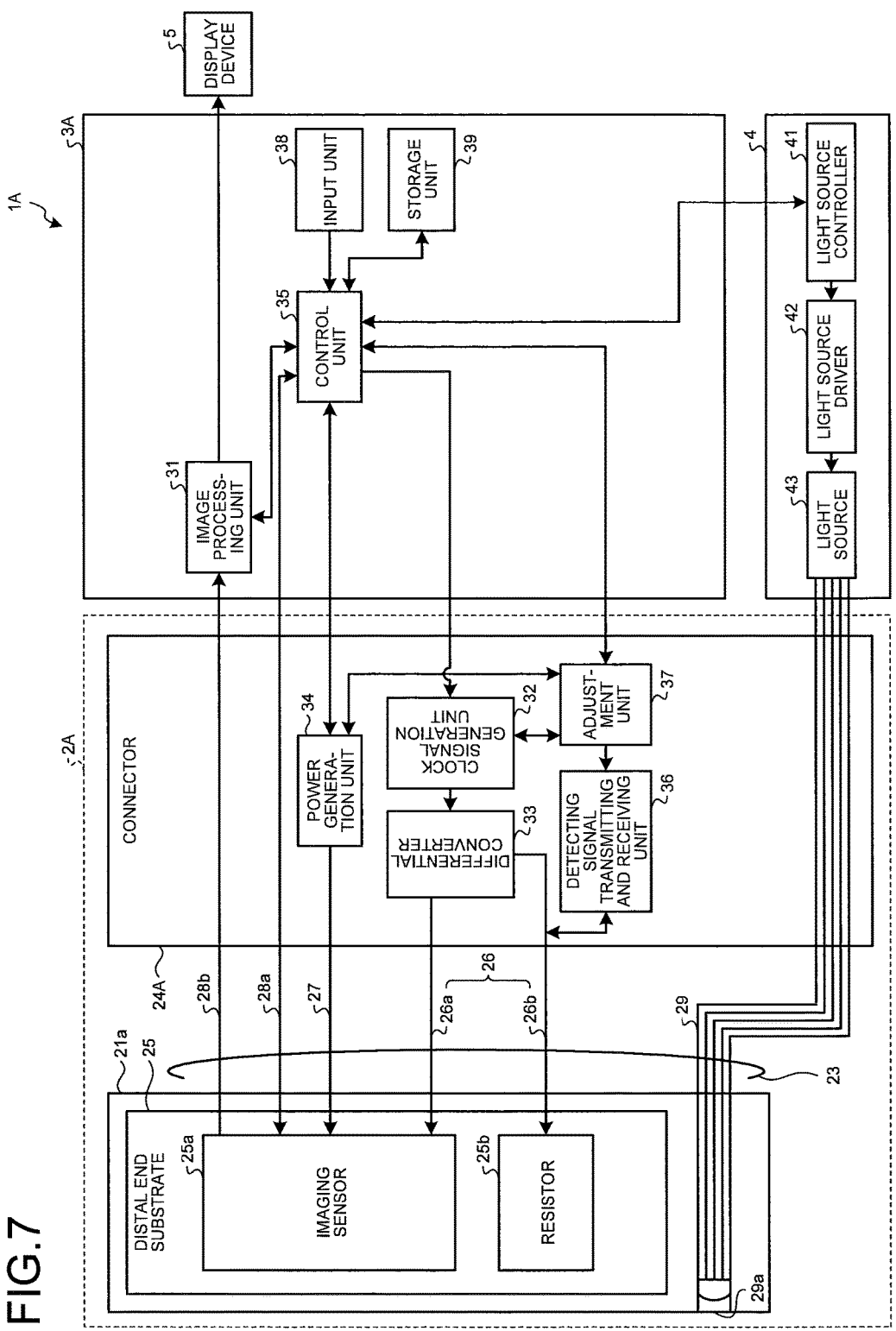
FIG. 7 is a block diagram schematically illustrating another configuration of the endoscope system according to the embodiment.

FIG. 7 is a block diagram schematically illustrating another configuration of the endoscope system according to the embodiment. As in an endoscope system 1A illustrated in FIG. 7, not a processing device 3A but a connector 24A of an endoscope 2A may be provided with the clock signal generation unit 32, the differential converter 33, the power generation unit 34, the detecting signal transmitting and receiving unit 36, and the adjustment unit 37, and adjust the value of the drive signal that is supplied to the endoscope 2A.

In the embodiment, the example in which the adjustment unit 37 adjusts both the clock signal and the power supply signal has been described. Alternatively, the adjustment unit 37 may change any one of the amplitude value of the clock signal and the voltage value of the power supply signal. Needless to say, the adjustment unit 37 may adjust characteristics of the various drive signals such as a control signal for the imaging sensor 25*a* and a drive signal for an actuator in addition to the clock signal and the power supply signal based on the acquired return time period T of the detecting signal or the cable length of the signal cable 26*b*.

Execution programs for the respective processes that are executed by the processing device 3 according to the embodiment and other components may be recorded and provided in a computer-readable recording medium such as a CD-ROM, a flexible disk, a CD-R, and a digital versatile disk (DVD) in an installable format or executable format file. Alternatively, the execution programs may be stored on a computer connected to a network such as the Internet, downloaded via the network, and provided. Alternatively, the execution programs may be provided or distributed via the network such as the Internet.

According to some embodiments, an imaging device includes a pair of signal lines configured to supply, as a differential signal, a clock signal that is one of a plurality of drive signals and configured such that impedance matching does not occur at a terminal of one of the pair of signal lines. The imaging device sends a detecting signal to the one of the pair of signal lines, and acquires a return time period that is a time period from when the detecting signal is sent until the detecting signal is reflected and returned from the terminal of the one of the pair of signal lines. The imaging device then adjusts characteristics of at least one of the plurality of drive signals based on the acquired return time period of the detecting signal. Therefore, it is possible to automatically adjust a value of the drive signal suitable for an endoscope for each endoscope while achieving a small diameter of the endoscope.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging device comprising:
an image sensor;
a processor comprising hardware, wherein the processor is configured to:
generate and output a plurality of drive signals for driving the image sensor; and
convert one of the plurality of drive signals into a differential signal; and
a pair of signal lines comprising:
a first signal line connected to the image sensor and configured to transmit the differential signal to drive the image sensor; and
a second signal line having the same length as the first signal line, wherein the second signal line is configured such that impedance matching does not occur at a terminal of the second signal line,
wherein the processor is further configured to:
send a detecting signal to the second signal line of the pair of signal lines; and
acquire a return time period that is a time period from when the detecting signal is sent until the detecting signal is reflected and returned from the terminal of the second signal line of the pair of signal lines; and
adjust characteristics of at least one of the plurality of drive signals based on the return time period.

2. The imaging device according to claim 1,
wherein the one of the plurality of drive signals is a clock signal,
wherein the processor is configured to:
convert the clock signal into the differential signal; and
adjust the characteristic of at least one of the plurality of drive signals by changing amplitude of the clock signal based on the return time period.

3. The imaging device according to claim 1,
wherein another one of the plurality of drive signals is a power supply signal for driving the image sensor, and
wherein the processor is configured to adjust the characteristic of at least one of the plurality of drive signals by changing voltage of the power supply signal based on the return time period.

4. A drive signal adjustment method that is performed by an imaging device comprising:
an image sensor;
a processor comprising hardware, wherein the processor is configured to:
generate and output a plurality of drive signals for driving the image sensor; and
convert one of the plurality of drive signals into a differential signal; and
a pair of signal lines comprising:
a first signal line connected to the image sensor and configured to transmit the differential signal to the image sensor; and
a second signal line having the same length as the first signal line, wherein the second signal line is configured such that impedance matching does not occur at a terminal of the second signal line,
wherein the method comprises:
the processor sending a detecting signal to the second signal line of the pair of signal lines;
the processor acquiring a return time period that is a time period from when the detecting signal is sent until the detecting signal is reflected and returned from the terminal of the second signal line of the pair of signal lines; and the processor adjusting characteristics of at least one of the plurality of drive signals based on the return time period.

5. An endoscope system comprising:

an insertion portion configured to be inserted into a subject;

an image sensor provided at a distal end of the insertion portion;

a processor comprising hardware to which the insertion portion is detachably connected, wherein the processor is configured to:

generate and output a plurality of drive signals for driving the image sensor; and convert one of the plurality of drive signals into a differential signal; and a pair of signal lines comprising:

a first signal line connected to the image sensor and configured to transmit the differential signal to drive the image sensor; and a second signal line having the same length as the first signal line, wherein the second signal line is configured such that impedance matching does not occur at a terminal of the second signal line, wherein the processor is further configured to:

send a detecting signal to the second signal line of the pair of signal lines; and acquire a return time period that is adjust characteristics of at least one of the plurality of drive signals based on a time period from when the detecting signal is sent until the detecting signal is reflected and returned from the terminal of the second signal line of the pair of signal lines;

adjust characteristics of at least one of the plurality of drive signals based on the return time period.

\* \* \* \* \*